(12) United States Patent
Chang et al.

(10) Patent No.: US 9,976,116 B2
(45) Date of Patent: May 22, 2018

(54) PROGRAMMABLE SYNTHETIC LYSIS SYSTEM FOR CONTROLLED RELEASE OF MACROMOLECULES

(71) Applicant: NANYANG TECHNOLOGICAL UNIVERSITY, Singapore (SG)

(72) Inventors: Matthew Wook Chang, Singapore (SG); Tat Ming Samuel Lo, Singapore (SG); Mui Hua Tan, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days. days.

(21) Appl. No.: 14/654,263

(22) PCT Filed: Dec. 13, 2013

(86) PCT No.: PCT/SG2013/000534
§ 371 (c)(1),
(2) Date: Jun. 19, 2015

(87) PCT Pub. No.: WO2014/098767
PCT Pub. Date: Jun. 26, 2014

(65) Prior Publication Data
US 2015/0322440 A1 Nov. 12, 2015

Related U.S. Application Data

(60) Provisional application No. 61/740,976, filed on Dec. 21, 2012.

(51) Int. Cl.
| | | |
|---|---|---|
| *C12N 15/70* | (2006.01) | |
| *C12N 15/74* | (2006.01) | |
| *C12N 1/06* | (2006.01) | |
| *A61K 48/00* | (2006.01) | |

(52) U.S. Cl.
CPC ............... *C12N 1/06* (2013.01); *C12N 15/70* (2013.01); *C12N 15/74* (2013.01); *A61K 48/00* (2013.01)

(58) Field of Classification Search
None
See application file for complete search history.

(56) References Cited

U.S. PATENT DOCUMENTS

| | | |
|---|---|---|
| 5,196,318 A | 3/1993 | Baldwin et al. |
| 2015/0209393 A1* | 7/2015 | Chang .................... A01N 37/46 424/93.2 |

OTHER PUBLICATIONS

Battesti et al., "The RpoS-Mediated General Stress Response in *Escherichia coli*," *Annual Review of Microbiology* 65:189-213, 2011.
Goeddel et al., "Expression in *Escherichia coli* of chemically synthesized genes for human insulin," *Proc Natl Acad Sci USA* 76(1):106-110, Jan. 1979.
Jeong et al., "Expression of ptsG encoding the major glucose transporter is regulated by ArcA in *Escherichia coli*," *J Biol Chem* 279(37):38513-38518, Sep. 10, 2004.
Jung et al., "Efficient production of polylactic acid and its copolymers by metabolically engineered *Escherichia coli*," *J Biotechnol* 151(1):94-101, 2011.
Lee et al., "Heterologous protein production in *Escherichia coli* using the propionate-inducible pPro system by conventional and auto-induction methods," *Protein Expression and Purification* 61:197-203, 2008.
Lo et al., "Designing a synthetic genetic circuit that enables cell density-dependent auto-regulatory lysis for macromolecule release," *Chemical Engineering Science* 103:29-35, Mar. 26, 2013.
Marschall et al., "Molecular analysis of the Regulation of csiD, a Carbon Starvation-inducible Gene in *Escherichia coli* that is Exclusively Dependent on $\sigma^s$ and Requires Activation by cAMP-CRP," *Journal of Molecular Biology* 276:339-353, 1998.
Metzner et al., "Multiple stress signal integration in the regulation of the complex $\sigma^s$-dependent csiD-ygaF-gabDTP operon in *Escherichia coli*," *Molecular Microbiology* 51(3):799-811, 2004.
Morita et al., "Programmed *Escherichia coli* Cell Lysis by Expression of Cloned T4 Phage Lysis Genes," *Biotechnology Progress* 17:573-576, 2001.
Nikel et al., "Poly(3-hydroxybutyrate) synthesis from glycerol by a recombinant *Escherichia coli* arcA mutant in fed-batch microaerobic cultures,"*Appl Microbiol Biotechnol* 77:1337-1343, Jan. 2008.
Nocadello et al., "The new pLAI (lux regulon based auto-inducible) expression system for recombinant protein production in *Escherichia coli*," *Microbial Cell Factories* 11:3, 2012.
Park et al., "Topological dynamics of holins in programmed bacterial lysis," *Proceedings of the National Academy of Sciences* 103(52):19713-19718, Dec. 26, 2006.
Pasotti, et al., "Characterization of a synthetic bacterial self-destruction device for programmed cell death and for recombinant proteins release," *J Biol Eng* 5:8, 2011.
Pesci et al., "Regulation of las and rhl quorum sensing in *Pseudomonas aeruginosa*," *J Bacteriol* 179(10):3127-3132, May 1997.
Rungrassamee et al., "Activation of glucose transport under oxidative stress in *Escherichia coli*," *Arch Microbiol* 190:41-49, 2008.
Saeidi et al., "Engineering microbes to sense and eradicate Pseudomonas aeruginosa, a human pathogen," *Molecular Systems Biology* 7:521, 2011, 11 pages.

(Continued)

*Primary Examiner* — Channing S Mahatan
(74) *Attorney, Agent, or Firm* — Seed IP Law Group LLP

(57) ABSTRACT

The present invention relates to an expression system or a recombinant cell comprising one or more nucleic acid constructs, wherein the one or more nucleic acid constructs comprise: (i) a first gene encoding for one or more protein(s) that activate a quorum sensing system; and (ii) a second gene encoding for one or more lytic protein(s) capable of forming a lesion in a host cell's membrane; wherein the first gene is under control of a first promoter and the second gene is under control of a second promoter, wherein the first promoter controlling the first gene is a carbon starvation-induced promoter and the second promoter is a quorum sensing system promoter induced by the quorum sensing system activated by one or more protein(s) encoded by the first gene as well as recombinant cells hosting such an expression system. Further encompassed is the use of the expression systems and cells of the invention for the expression of gene products of interest and the respective methods of use.

27 Claims, 9 Drawing Sheets

(56) References Cited

OTHER PUBLICATIONS

Swartz, "Advances in *Escherichia coli* production of therapeutic proteins," *Curr Opin Biotechnol* 12:195-201, 2001.
Tsao et al., "Autonomous induction of recombinant poteins by minimally rewiring native quorum sensing regulon of *E. coli*," *Metabolic Engineering* 12:291-297, 2010.
Yun et al., "Development of a novel vector system for programmed cell lysis in *Escherichia coli*," *J Microbiol Biotechnol* 17(7):1162-1168, 2007.

\* cited by examiner a b las quorum sensing based expression system

Controllable synthetic lysis system

SEQUENCE LISTING

```
<160> NUMBER OF SEQ ID NOS: 5

<210> SEQ ID NO 1
<211> LENGTH: 217
<212> TYPE: DNA
<213> ORGANISM: Escherichia coli

<400> SEQUENCE: 1
ctgttctcta atgttaactc cccctaacct gttgctttag ttattcattt cctgtctcac      60
tttgccttaa taccctacgt taaatgttac taatttgttg cttttgatca caataagaaa     120
acaatatgtc gcttttgtgc gcatttttca gaaatgtaga tatttttaga ttatggctac     180
gaaatgagca tcgccatgtc accctacatc tcataag                              217

<210> SEQ ID NO 2
<211> LENGTH: 16
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: (6)..(11)
```

<223> OTHER INFORMATION: N is any nucleic acid

<400> SEQUENCE: 2
tgtgannnnn ntcaca                                              16

<210> SEQ ID NO 3
<211> LENGTH: 73
<212> TYPE: DNA
<213> ORGANISM: Pseudomonas aeruginosa

<400> SEQUENCE: 3
ggttcaccga aatctatctc atttgctagt tataaaatta tgaaatttgc ataaattctt    60
cagcttccta ttt                                                 73

<210> SEQ ID NO 4
<211> LENGTH: 606
<212> TYPE: DNA
<213> ORGANISM: Pseudomonas aeruginosa

<400> SEQUENCE: 4
atgatcgtac aaattggtcg gcgcgaagag ttcgataaaa aactgctggg cgagatgcac    60
aagttgcgtg ctcaagtgtt caaggagcgc aaaggctggg acgttagtgt catcgacgag   120
atggaaatcg atggttatga cgcactcagt cctattacca tgttgatcca ggaagatact   180
cctgaagccc aggttttcgg ttgctggcgc attctcgata ccactggccc ctacatgctg   240
aagaacacct tcccggagct tctgcacggc aaggaagcgc cttgctcgcc gcacatctgg   300
gaactcagcc gtttcgccat caactctgga cagaaaggct cgctgggctt ttccgactgt   360
acgctggagg cgatgcgcgc gctggcccgc tacagcctgc agaacgacat ccagacgctg   420
gtgacggtaa ccaccgtagg cgtggagaag atgatgatcc gtgccggcct ggacgtatcg   480
cgcttcggtc cgcacctgaa gatcggcatc gagcgcgcgg tggccttgcg catcgaactc   540
aatgccaaga cccagatcgc gctttacggg ggagtgctgg tggaacagcg actggcggtt   600
tcatga                                                        606

<210> SEQ ID NO 5
<211> LENGTH: 723
<212> TYPE: DNA
<213> ORGANISM: Pseudomonas aeruginosa

<400> SEQUENCE: 5
atggccttgg ttgacggttt tcttgagctg gaacgctcaa gtggaaaatt ggagtggagc    60
gccatcctcc agaagatggc gagcgacctt ggattctcga agatcctgtt cggcctgttg   120
cctaaggaca gccaggacta cgagaacgcc ttcatcgtcg caactaccc ggccgcctgg    180 cgcgagcatt acgaccgggc tggctacgcg cgggtcgacc cgacggtcag tcactgtacc   240
cagagcgtac tgccgatttt ctgggaaccg tccatctacc agacgcgaaa gcagcacgag   300
ttcttcgagg aagcctcggc cgccggcctg gtgtatgggc tgaccatgcc gctgcatggt   360
gctcgcggcg aactcggcgc gctgagcctc agcgtggaag cggaaaaccg ggccgaggcc   420
aaccgtttca tagagtcggt cctgccgacc ctgtggatgc tcaaggacta cgcactgcaa   480
agcggtgccg gactggcctt cgaacatccg gtcagcaaac cggtggttct gaccagccgg   540

```
gagaaggaag tgttgcagtg gtgcgccatc ggcaagacca gttgggagat atcggttatc    600
tgcaactgct cggaagccaa tgtgaacttc catatgggaa atattcggcg gaagttcggt    660
gtgacctccc gccgcgtagc ggccattatg gccgttaatt tgggtcttat tactctctaa   720
taa                                                                  723
```

PROGRAMMABLE SYNTHETIC LYSIS SYSTEM FOR CONTROLLED RELEASE OF MACROMOLECULES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_486USPC_SEQUENCE_LISTING.txt. The text file is 3.3 KB, was created on Jun. 17, 2015, and is being submitted electronically via EFS-Web.

FIELD OF THE INVENTION

The invention lies in the field of prokaryotic recombinant lysis systems designed for controlled released of macromolecules at high cell density.

BACKGROUND OF THE INVENTION

Prokaryotic cells have been widely exploited in genetic engineering in the manufacturing of useful products (e.g., for the production of food, drinks, drugs, agricultural chemicals and polymers). Prokaryotic cells such as *Escherichia coli* (*E. coli*), a well-characterized and well-studied organism, have been used as host organisms in biotechnology. Owing to its physiological simplicity and wide-array of molecular tools available, *E. coli* can be easily genetically manipulated for bio-production of useful and valuable compounds. Useful as it seems, *E. coli* however is limited by its inherent inability to export macromolecules such as therapeutic proteins (e.g. human-derived insulin [1]) and valuable bio-polymers (e.g. polylactic acid [2]) out of the cell.

As such, industrial players may have to resort to mechanical (e.g. ultrasonication), chemical (e.g. detergent) or enzymatic (e.g. lysozyme) treatment to disrupt the bacteria cells for macromolecule extraction [3]. These methods have proved to be useful, but require additional purchase of expensive reagents and equipments.

Naturally occurring lytic and temperate bacteriophages have the ability to provoke host cell lysis through the expression of specific proteins during the lytic cycle. In many phages, like the T4 phage and the lambda phage, these proteins have been identified and widely studied. In particular, holins form stable and non-specific lesions in the cytoplasmic membrane that allow the lysozymes to gain access to the peptidoglycan layer. Lysozymes are generally soluble proteins with one or more muralytic activities against the three different types of covalent bonds (glycosidic, amide, and peptide) of the peptidoglycan polymer of the cell wall. The combined work of holin and lysozyme results in the degradation of the two cell membranes of gram-negative bacteria, thus causing cell lysis. Antiholin is a third protein involved in this process as it inhibits holin and is responsible for the regulation of its activity. The described lytic mechanism can be exploited for the release of useful recombinant proteins which cannot be secreted by the engineered host strain.

In an attempt to improve the efficiency and economy of the downstream processing for product extraction, Morita and colleagues [4] had introduced the concept of programmed cell lysis by having *E. coli* express T4 bacteriophage lytic proteins. The lytic proteins such as holin are responsible for forming a lesion in the host cell membrane [5]. Though the use of lytic protein certainly eases and simplifies the cell disruption process, this method however, still involves supplementary chemical inducers to regulate the lytic protein expression which can be quite costly for industrial scale-up.

To address this challenge, Yun et al. [6] proposed the use of an inducible promoter that does not require additional materials for induction. This proposed promoter, a mutated P1 promoter of ptsG, the gene for major glucose PTS transporter in *E. coli*, was found to be up-regulated upon glucose exhaustion. By placing the lysis genes under the control of the mutant ptsG P1 promoter (ptsGPL), this approach ensures that there is sufficient cell growth before cell lysis and avoids premature lysis. Though this approach has the merit of enabling *E. coli* to release product macromolecules at high cell density without any additional step for cell disruption, the authors reported that this method did not lead to a huge reduction in the *E. coli*'s viability after glucose exhaustion due to the low activity of ptsGPL promoter. Further, a closer look into the ptsG promoter suggested that this promoter can be regulated by factors other than glucose. Other factors such as oxygen concentration [7] and oxidative stress [8] are known to influence the activity ptsG promoter. Hence, the use of ptsG promoter is plagued by its low promoter activity and poor specificity, which may hamper its use in industrial settings.

An alternative approach to the glucose-regulated ptsG promoter is the use of the auto-regulatory quorum sensing based expression system, such as the lux regulon from *Vibrio fischeri* [9]. The quorum sensing system enables users to link recombinant gene expression to population density since the cells would produce a specific signal molecule, N-acyl-homoserine lactone (AHL) that would up-regulate the promoter once the threshold AHL concentration is reached. Such a system is auto-inducible, and it allows cells to activate recombinant gene expression at high cell density. Further, the quorum sensing system can be organized in a way that a positive feedback loop is created for amplifying protein expression. However, this auto-regulatory system is designed in such a way that the users may find it difficult to assert control over the threshold cell density at which the system is activated. To assume control over the activating cell density, users may have to perform trial and error to select the best combination of synthetic constitutive promoter and ribosome binding site for tuning the expression of AHL synthetase, the enzyme responsible for producing AHL from metabolite S-adenosylmethionine. This brute-force method is laborious and time-consuming.

Thus, there remains need in the art for programmable cell lysis systems that overcome the drawbacks of existing technologies.

SUMMARY OF THE INVENTION

The inventors of the present invention have surprisingly found that the above-formulated need can be met by an expression system that is regulated by two promoters, with the first promoter being activated by a carbon starvation signal and controlling a gene involved in activating a quorum sensing system and the second promoter being activated by the quorum sensing system controlled by the first promoter and controlling a gene that encodes for a gene product that is involved in the lysis of the host cell.

In a first aspect, the present invention therefore relates to an expression system comprising one or more nucleic acid constructs, wherein the one or more nucleic acid constructs comprise:

(i) a first gene encoding for one or more protein(s) that activate a quorum sensing system; and
(ii) a second gene encoding for one or more lytic protein(s) capable of forming a lesion in a host cell's membrane;

wherein the first gene is under control of a first promoter and the second gene is under control of a second promoter, wherein the first promoter controlling the first gene is a carbon starvation-induced promoter and the second promoter is a quorum sensing system promoter induced by the quorum sensing system activated by one or more protein(s) encoded by the first gene.

A second aspect of the invention includes a recombinant cell comprising an expression system of the invention.

A third aspect of the invention includes a method for the recombinant expression of a gene product of interest, comprising cultivating the recombinant cell of the invention under conditions that allow the expression of the gene product of interest and lysis of the recombinant cell.

A fourth aspect of the invention includes use of the recombinant cell of the invention for the recombinant expression of a gene product of interest.

Further embodiments will be apparent to a person skilled in the art with reference to the following and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following drawings.

DETAILED DESCRIPTION

Figure 1:
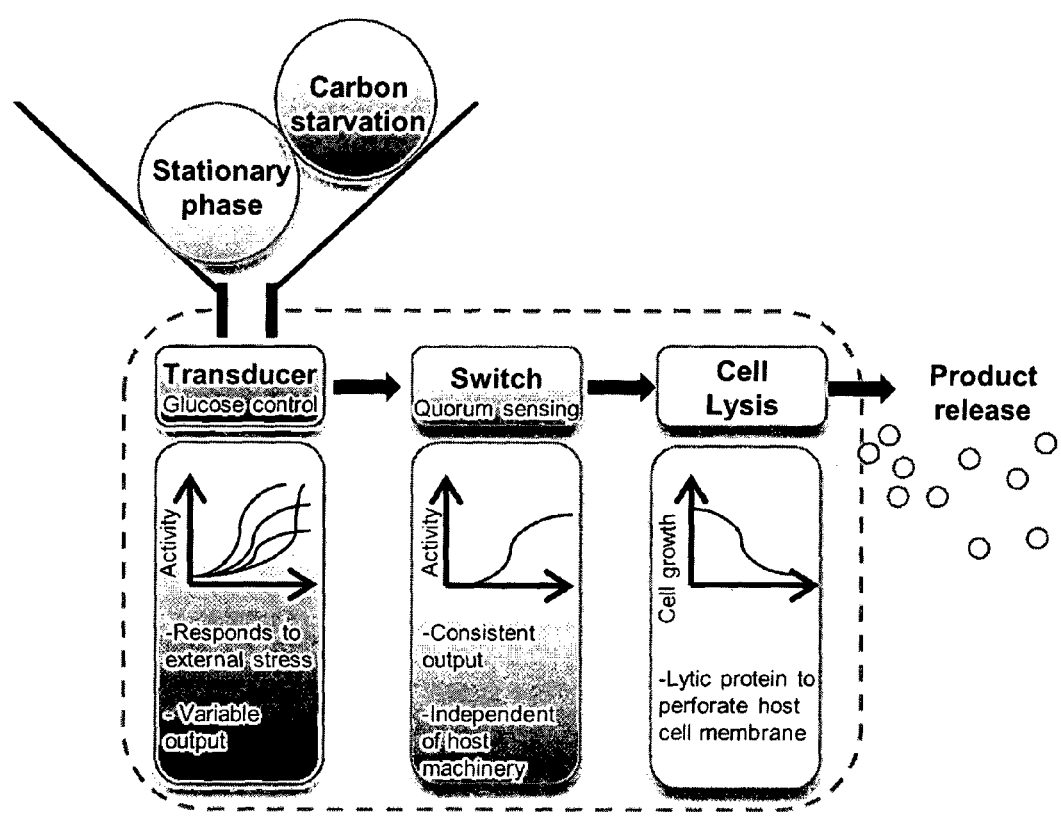
FIG. 1: An overview of a programmable synthetic lysis system for the controlled-released of macromolecules.

A new method for gene expression is espoused. It is an autonomous regulated system that is capable of autolysis based on desired features such as carbon concentration and cell density in the media. The expression system comprising a carbon starvation-induced and/or a stationary phase-induced promoter that act as a transducer. The activated transducer further activates a second promoter that acts as a switch.

Specifically, a first aspect of the invention relates to an expression system comprising one or more nucleic acid constructs, wherein the one or more nucleic acid constructs comprise:
(i) a first gene encoding for one or more protein(s) that activate a quorum sensing system; and
(ii) a second gene encoding for one or more lytic protein(s) capable of forming a lesion in a host cell's membrane;

wherein the first gene is under control of a first promoter and the second gene is under control of a second promoter, wherein the first promoter controlling the first gene is a carbon starvation-induced promoter and the second promoter is a quorum sensing system promoter induced by the quorum sensing system activated by one or more protein(s) encoded by the first gene.

"One or more", as used herein relates to at least 1 and includes 1, 2, 3, 4, 5, 6, 7, 8, 9 and more. Any function assigned to the "one or more" species may be achieved independently by each of the species or achieved by the combination of the more than one species.

The expression system may be designed to operate in vitro or may be a cell based expression system. In a preferred embodiment, the expression system is a prokaryotic cell based system.

The term "nucleic acid construct" as used herein refers to a nucleic acid molecule that includes a given sequence. The nucleic acid may be DNA, RNA, DNA:RNA hybrids, PNA and the like, but preferably is DNA. The construct can be an expression vector for expression of a protein encoded by a recombinant gene carried by said vector, a plasmid, cosmid, or artificial chromosome. A preferred vector is a vector that can self-replicate and express a given nucleic acid sequence included therein.

The term "first gene" and "second gene", as used herein, relate to nucleic acid sequences that encode for one or more gene products of the given functionality. Accordingly, the first gene may comprise one or more genes with each of said genes encoding for a separate gene product. This applies similarly to the second gene. Both, the first and the second gene may comprise additional non-coding sequence stretches required for transcription and translation of the respective coding sequences besides the first and second promoter.

Generally, the nucleic acid constructs may additionally comprise further regulatory elements, such as enhancers or silencers, all of which are well known to those skilled in the art.

Quorum sensing is the regulation of gene expression in response to fluctuations in cell-population density. Quorum sensing bacteria (Gram-positive and Gram-negative) produce and release chemical signal molecules called autoinducers that increase in concentration as a function of cell density. The detection of a minimal threshold stimulatory concentration of an autoinducer leads to an alteration in gene expression.

In one embodiment, the first promoter is a glucose-dependent carbon starvation-induced promoter and/or a stationary growth phase-induced promoter. It is understood, that glucose-dependency is used for exemplary purposes only and carbon starvation may also be controlled by alternative carbon sources. The nature of the carbon source may depend on the type of host organism used, but commonly includes other saccharides, alcohols and derivatives thereof.

In preferred embodiments, the first promoter is a csiD promoter (csiDp) from *E. coli* and may comprises a nucleic acid sequence having at least 70, preferably at least 80, more preferably at least 90, most preferably at least 95% or 100% sequence identity with the nucleic acid sequence set forth in SEQ ID NO: 1. The term "percent sequence identity" as used herein in relation to amino acid and nucleotide sequences means that a residue of a given molecule is identical to that at the corresponding position of a reference molecule in the percentage indicated.

The csiDp is commonly activated by the presence of the carbon starvation signal molecule complex cAMP-CRP and/or optionally the stationary phase signal molecule stress sigma 38 factor (RpoS). More preferably, the csiDp is activated by the presence of both the signaling molecules cAMP-CRP, induced by carbon starvation, and RpoS, induced by stationary growth phase-related stress.

The carbon starvation-induced promoter is derived from a class of genes (the starvation genes) that are switched on in a metabolically sluggish state. While most other types of gene expression are greatly attenuated, these genes exhibit a high level of expression in this state. For example, at the onset of starvation *Escherichia coli* undergoes a temporally ordered program of starvation gene expression involving 40-80 genes. Two classes of genes are induced upon carbon starvation: the cst genes, requiring cyclic AMP, and the pex genes, not requiring this nucleotide for induction. The cst genes are not involved in the development of the resistant state and are concerned with escape from starvation, while the pex gene induction appears to be associated with resistance. Many of the latter (e.g. heat shock and oxidation resistance genes, and some utilize minor, stationary-phase-specific sigma factors for induction during starvation) are induced in response to a variety of starvation conditions. The starvation promoters are thus potentially useful for selective expression of desired genes in metabolically sluggish populations, e.g. in high-density industrial fermentations and in situ bioremediation.

The stationary phase signaling molecule RpoS sigma factor is also known as E sigma 38. While this expression product is primarily known to activate stress related genes in the stationary phase of bacterial cell growth the inventors have been able to use the onset of transcription of the RpoS sigma factor after the exponential growth phase of a bacterial population as a promoter to activate non-stress genes at a time that cell density is stable. In this way expression system is able to be activated by RpoS and can be switched on in a prokaryotic cell when cell population density is optimal for production.

Many microbes have a regulatory process called "catabolite repression". During growth on a preferred carbon source, transcription of genes involved in the catabolism of other carbon sources is prevented. In Enterobacteriaciae (such as *E. coli*), this process is mediated by the CRP protein (Catabolite regulation protein). The presence or absence of glucose determines the concentration of cAMP, the small molecule effector that determines the activity of CRP. cAMP-CRP activates expression of many genes. cAMP-CRP activates transcription by binding to specific sites on the DNA where it directly interacts with RNA Polymerase. cAMP-CRP binding sites can be located approximately 61 bp upstream of the promoter (Class I CRP-binding sites), 41 bp upstream of the promoter (Class II CRP-binding sites), or >90 bp upstream of the promoter (Class III CRP-binding sites). The cAMP-CRP consensus binding site is: TGTGA-N6-TCACA (SEQ ID NO. 2). There are many variations on this sequence that influence the affinity of cAMP-CRP binding to different sites, resulting in a hierarchy of cAMP-CRP activation of different operons. The relative affinity of cAMP-CRP for binding sites on the *E. coli* chromosome varies over 50-fold. When glucose is absent, the concentration of enzyme IIIglc remains high. Enzyme IIIglc-P activates adenylate cyclase to produce cAMP. Thus, the cAMP increases in the absence of glucose.

In various embodiments of the expression system of the invention, the first gene which is under control of the first promoter encodes for one or more signaling molecules capable of activating the quorum sensing system upon reaching a threshold concentration. Alternatively, the activation of the quorum sensing system may be indirect in that the first gene encodes for one or more enzymes that produce said signaling molecules that are capable of activating said quorum sensing system upon reaching a threshold concentration. The one or more enzymes that produce said signaling molecules may comprise N-acyl-homoserine-lactone synthetase (AHL synthetase) and the signaling molecule may be N-acyl-homoserine-lactone (AHL).

In various embodiments, the second promoter is induced upon reaching a threshold concentration of a signalling molecule of the quorum sensing system activated by one or more protein(s) encoded by the first gene. The quorum sensing system may be the LasI/LasR quorum sensing system from *Pseudomonas aeruginosa*. In such embodiments, the second promoter may be the lasI gene promoter from *Pseudomonas aeruginosa*, the lasI gene promoter being activated by AHL produced by the first gene product upon reaching a certain AHL threshold concentration. In various embodiments, the second promoter is a Las1 promoter (Las1p) from *P. aeruginosa* and may comprises a nucleic acid sequence set forth in SEQ ID NO. 3 having at least 70, preferably at least 80, more preferably at least 90, most preferably at least 95% sequence identity with the nucleic acid sequence set forth in SEQ ID NO: 3.

In one embodiment where the quorum sensing system is the LasI/LasR quorum sensing system from *Pseudomonas aeruginosa* and the second promoter is the lasI gene promoter from *Pseudomonas aeruginosa*, the first gene is the lasI gene and encodes the acylhomoserine lactone (AHL) synthase LasI that produces N-3-oxo-dodecanoyl-L-homoserine lactone (3-O—C12-HSL) from the substrates 3-oxo-C12-acyl-carrier protein (acyl-ACP) and S-adenosyl-L-methionine may comprises a nucleic acid sequence set forth in SEQ ID NO. 4 having at least 70, preferably at least 80, more preferably at least 90, most preferably at least 95% sequence identity with the nucleic acid sequence set forth in SEQ ID NO: 4 provided the lasI produces an active AHL synthase.

In various embodiments, the second gene encodes bacteriophage lytic proteins, preferably T4 bacteriophage lytic proteins, more preferably holin and/or lysozyme and, optionally, antiholin.

During the lytic cycle of most bacteriophages, two proteins, an endolysin and a holin, are essential for host lysis by bacteriophage. Endolysin is the term for muralytic enzymes that degrade the cell wall; e.g. T4 bacteriophage lytic protein is required to allow the phage's lysozyme to reach the murein layer of the cell envelope and cause lysis. Holins are small membrane proteins that accumulate in the membrane until, at a specific time that is "programmed" into the holin gene, the membrane suddenly becomes permeabilized to the fully folded endolysin.

In a preferred embodiment, the expression system comprises two or more nucleic acid constructs, wherein the first gene and the first promoter are located on a first nucleic acid construct, and the second gene and the second promoter are located on a second nucleic acid construct.

In one particular embodiment, the expression system of the invention further comprises a third gene encoding for a gene product of interest. In various embodiments, the third gene may be located on the same nucleic acid construct as the first and/or second gene. Alternatively, the third gene can be located on a separate nucleic acid construct, i.e. a nucleic acid construct neither comprising the first gene nor the second gene. The gene product of interest may be a therapeutic or non-therapeutic protein, a biopolymer, DNA plasmid or component thereof. The third gene may be under the control of a third promoter which may be constitutively active or inducible. Suitable expression constructs and promoters are known in the art and may be selected by those skilled in the art based on their general knowledge essentially independent from the genes and promoters that control cell auto-lysis, as long as it is ensured that the gene product of interest has been produced at the desired concentration upon lysis of the cell.

A second aspect of the invention is a recombinant cell comprising an expression system of the invention as described above in the first aspect.

The recombinant cell may be a cell-based expression system. In a preferred embodiment, the recombinant cell is a genetically engineered prokaryotic cell. In various embodiments, the prokaryotic cell is an *E. coli* cell.

In various embodiments, the first promoter is an autologous promoter, i.e. a promoter that naturally occurs in the host cell. In various embodiments, the first promoter is a glucose-dependent carbon-starvation induced promoter and/or a stationary growth phase induced promoter. Most preferably, the first promoter is csiD promoter from *E. coli* as described herein. In such embodiments, the first gene controlled by the first promoter is a gene not naturally under control of said promoter, preferably a heterologous gene.

In one embodiment of the recombinant cell of the present invention the carbon starvation signal molecule is CRP-cAMP complex and the stationary phase signal molecule is stress sigma 38 factor (RpoS). Both in combination activate the first promoter and trigger expression of the first gene. These signalling molecules are disclosed as exemplary triggers of the first promoter and it will be apparent for those skilled in the art that dependent on the first promoter employed different signalling molecules will be necessary. It is however preferred that these signalling molecules that regulate the first promoter are autologous molecules that are automatically produced by the host cell under carbon starvation conditions and, optionally, stationary phase growth conditions.

In various embodiments, the first gene encodes for one or more signalling molecules capable of activating said quorum sensing system upon reaching a threshold concentration. Optionally, the activation of the quorom sensing system may be indirect in that the first gene encodes for one or more enzymes that produce said signaling molecules that capable of activating said quorum sensing system upon reaching a threshold concentration. This means that the gene product of the first gene may be a transcription factor itself in that it binds to and activates the second promoter or, alternatively, is part of a signalling cascade that leads to activation of the second promoter. As the second promoter is a promoter derived from a quorum sensing system, in preferred embodiments it is controlled by AHL levels. Accordingly, it is preferred that the first gene encodes for one or more enzymes that produce AHL, for example N-acyl-homoserine-lactone synthethase (AHL synthethase). In those embodiments, the signaling molecule is N-acyl-homoserine-lactone (AHL).

In various embodiments, the second promoter is induced upon reaching a threshold concentration of a signaling molecule of the quorum sensing system activated by one or more protein(s) encoded by the first gene.

The quorum sensing system employed preferably is or comprises a heterologous quorum sensing system. This may help to avoid interference with cellular pathways.

In various embodiments, the second gene encoding a cell lysis signal or molecule is a heterologous gene.

It is preferred that the quorum sensing system employed, in particular the promoter, and the second gene encoding proteins involved in auto-lysis of the host cell are not naturally associated with each other.

In one particular embodiment, the quorum sensing system can be a rhl quorum sensing system. In a preferred embodiment, the quorum sensing system is a las quorum sensing system. The quorum-sensing systems regulate virulence gene expression in *Pseudomonas aeruginosa*. The las system consists of a transcriptional activator, LasR, and the LasI enzyme, which directs the synthesis of the autoinducer N-(3-oxododecanoyl) homoserine lactone (PAI-1). Induction of lasB (encoding elastase) and other virulence genes requires LasR and PAI-1. The rhl system consists of a putative transcriptional activator, RhlR, and RhlI, which directs the synthesis of N-butyryl homoserine lactone (PAI-2). Rhamnolipid production in *P. aeruginosa* has been reported to require both the rhl system and rhlAB (encoding a rhamnosyltransferase).

In one specific embodiment, the second promoter is a lasI promoter which controls the expression of lytic protein(s). In such embodiments, the signalling molecule controlling second promoter activation is AHL. Upon reaching a threshold concentration of the signaling molecule, the quorum sensing system promoter is activated and the expression of the lytic proteins under control of the second promoter is started. The lytic protein(s) encoded by the second gene are capable of forming a lesion in the recombinant cell's membrane and/or cell wall, thus triggering cell autolysis.

The "lytic protein(s) capable of forming a lesion in a host cell's membrane" relates to one or more proteins that are capable and sufficient for inducing auto-lysis of the host cell in which they are expressed. In case said host cell comprises one or more outer membranes and, optionally, a cell wall, these proteins create a lesion in at least the innermost membrane of the cell sheath, preferably all outer membranes and the cell wall.

In a third aspect, present invention provides a new method for recombinant gene expression of gene product of interest, including cultivating the recombinant cell according to the current invention under conditions that allow the expression of the gene product of interest and lysis of the recombinant cell.

In such embodiments, the recombinant cell comprises a further nucleotide sequence encoding the gene product of interest, for example in form of a third gene, and expression of said gene product of interest is controlled such that product levels are at a desired level upon lysis of the cell and release of the product.

This method of gene expression is capable of regulating the protein expression level based on desired features such as substrate concentration and cell density. By introducing transducer (autologous carbon starvation-induced promoter) and switch (heterologous lasI promoter) the means for attaining optimal performance in dynamic biological systems are provided, as said system allows recombinant cell autolysis at a desired time to release macromolecules of interest.

The method may further comprise isolating the gene product of interest, e.g. a macromolecule, from the cultivating medium after lysis of the recombinant cell has occurred. Techniques for such isolation are widely known in the field and include, for example, chromatography, centrifugation, filtration and the like.

An expression system (FIG. 1) that enables recombinant cell e.g. *E. coli* to auto-lyse during stationary phase at high cell density is shown in present invention, yet offers users the ability to choose the activating threshold cell density. Towards this goal, an improved alternative to the ptsG promoter which is the promoter for csiD, a carbon starvation-induced gene in *E. coli*, to act as a transducer to activate the switch for cell lysis is used. The csiD promoter (csiDp) is activated exclusively upon carbon starvation and stationary phase [10-12].

The engineered auto-lytic cells offer users significant cost savings in downstream processes as compared to traditional cell disruption methods such as ultrasonication, ball-milling and chemical disruption that would require costly equipment and other expensive chemical reagents. Further, compared to existing bio-lytic methods which use costly inducers such as IPTG for lysis gene activation, the method of the present invention eliminates the need for external inducers and can bring considerable material cost savings in the industrial bioprocessing. The system of the present invention would activate lytic protein production only at high cell density when the nutrients are depleted.

Figure 2:
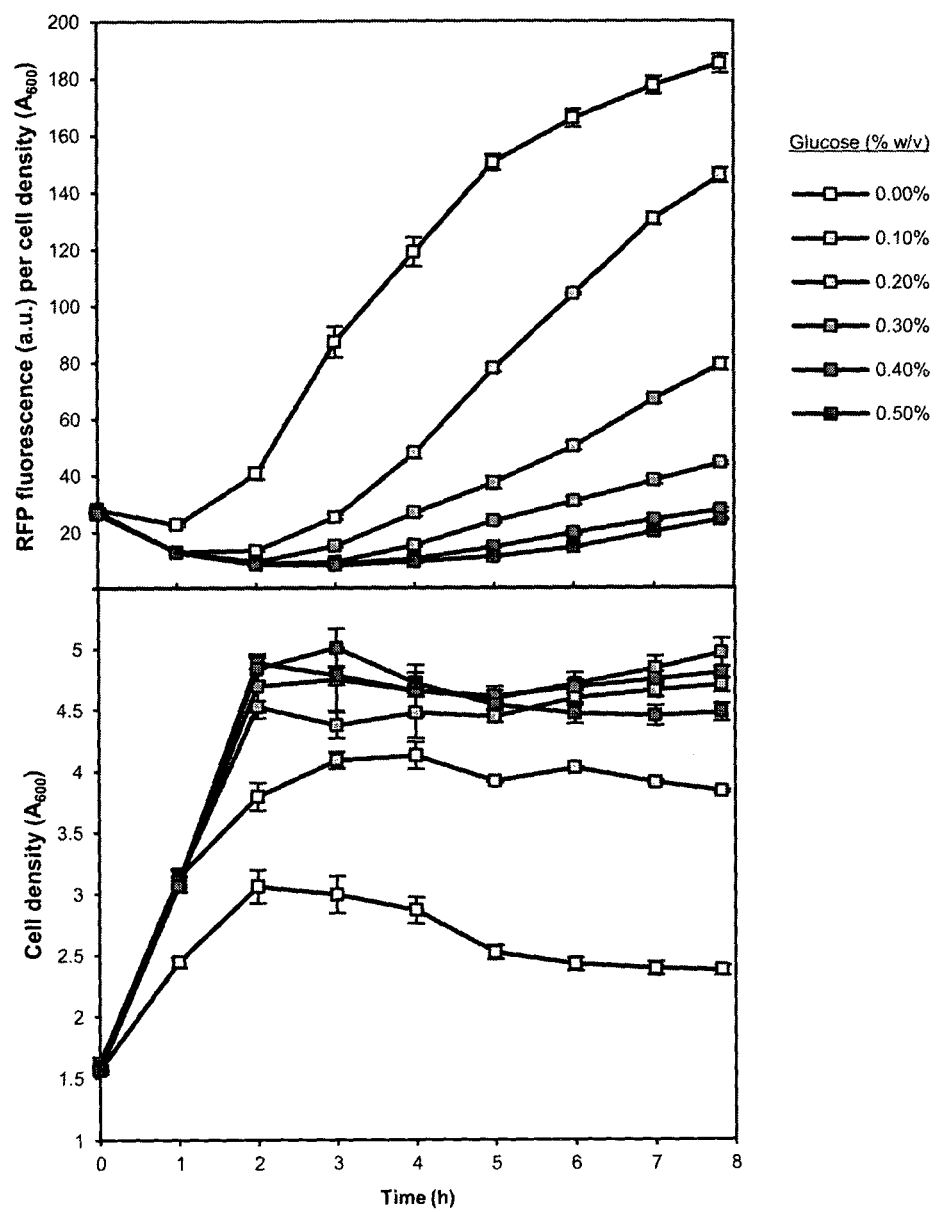
FIG. 2: Characterization of the construct with different glucose inputs. Recombinant cell reaches stationary phase after 2 hours inoculation and releases RFP fluorescence lysate in stationary phase. Higher glucose input increases cell density but produces lower lytic protein output.

Engineered cells auto-lyse and release the macromolecular products when they reach stationary phase and carbon exhaustion (FIG. 2). By doing so, the cells eliminate any additional cell disruption step required in bioprocessing. This saves time and materials, which in turn improves and simplifies the downstream bioprocessing.

Figure 3:
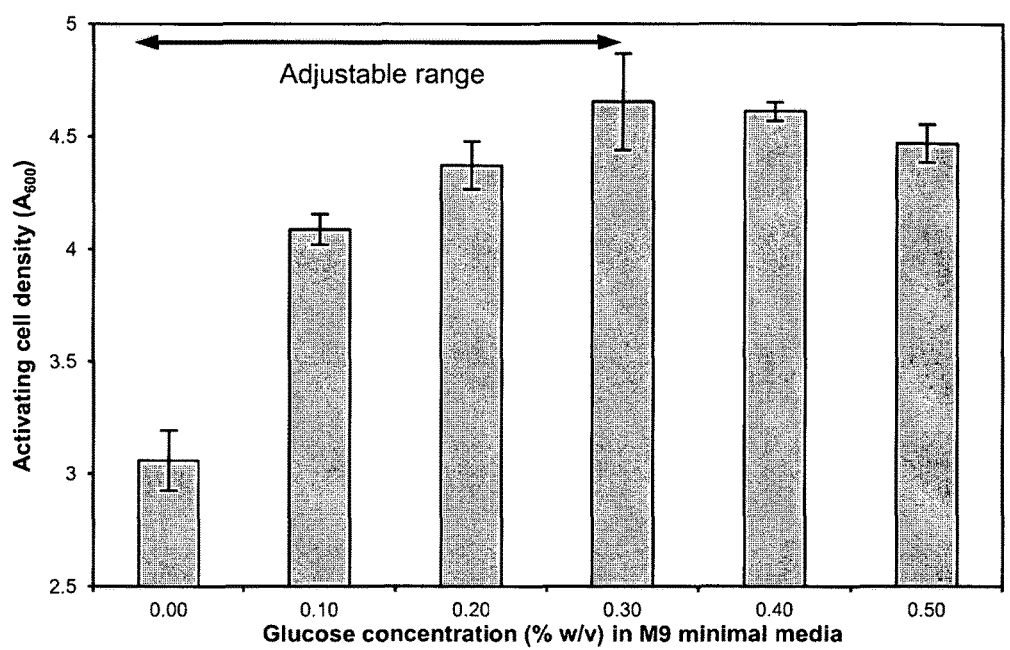
FIG. 3: The designed construct allows a controllable activated cell density with 0-0.3% (w/v) glucose concentration in M9 minimal media. Starting from the lowest glucose concentration (0%), cell density (optical density is determined by $A_{600}$) increases step-wise starting from 0.1% glucose concentration and reaching maximum cell density at 0.3% glucose concentration. Cell density maintains at a slightly lower level when 0.4% and 0.5% glucose concentrations in M9 minimal media are used. The result demonstrated that 0-0.3% glucose concentration appear to be in an adjustable range.

In existing bio-lytic devices such as the quorum sensing regulated lysis, users are unable to control at what amount of cell density would trigger cellular lysis. For this invention, a genetic circuit that offers users a choice to determine the amount of triggering cell density through the use of glucose is developed. Towards this aim, a stationary phase carbon starvation promoter, csiDp which allows users to adjust the amount of glucose in the growth medium necessary to reach the targeted cell density (FIG. 3) is adopted.

Figure 4:
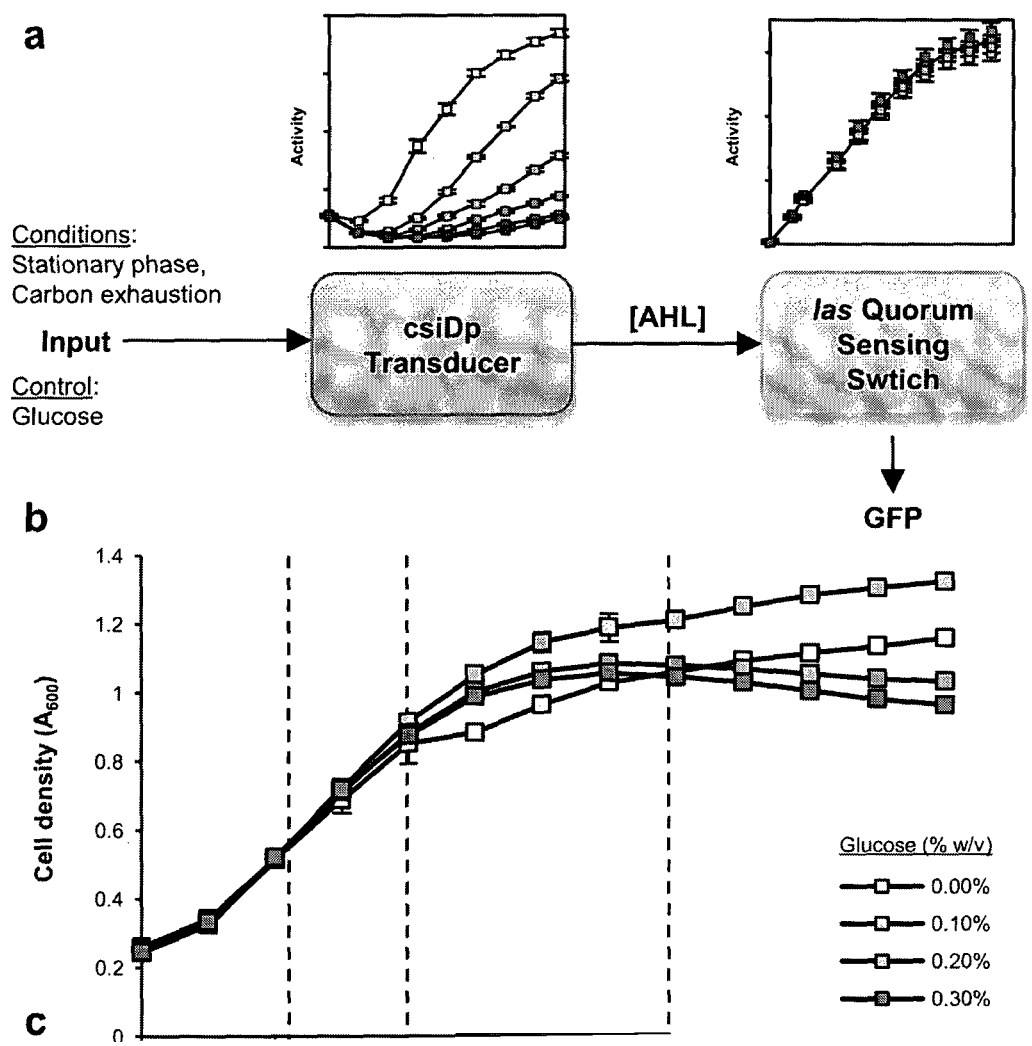
FIG. 4: (a) Schematic of the combination of csiDp transducer and lasQS switch, which was used to regulate GFP expression as a proof of concept. (b-c) Characterized behavior of the csiDp-regulated 3-O—C12-HSL (AHL) synthetase, LasI coupled with the las quorum sensing switch, with cell growth indicated in (b) and GFP expression in (c). The combined csiDp-las system enabled the users to control GFP output expression through different glucose inputs. A concentration of 0-0.1% (w/v) glucose leads to a consistent elevated GFP output, while 0.2-0.3% (w/v) glucose represses the system. The high initial GFP expression was due to E. coli cells being diluted from stationary phase when they were first grown unrepressed in LB medium.

Together with a las quorum sensing system, users are able to achieve the same amount of lytic protein expression regardless of different activating cell densities for glucose concentration ranging from 0-0.1% (FIG. 4). If users decide to put the lytic process on hold, glucose can be added from 0.2% and above to the medium for repress the system. Through varying the glucose concentration in the medium, the system of the present invention presents an "On/Off" option to the users that is cheap and easy to use.

It is envisioned that the present invention is highly applicable in the industrial production of therapeutic proteins. Therapeutic protein such as insulin or bovine growth hormone can be produced with the proposed gene expression method of the present invention. Further, non-therapeutic protein, bio-polymer such PLA (polylactic acid), 1,3-propanediol or PHB (poly-3-hydroxybutayrate) can be produced.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

By "about" in relation to a given numerical value, such as for temperature and period of time, it is meant to include numerical values within 10% of the specified value.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. It is to be understood that these examples are for illustrative purposes only and are not to be construed to limit the scope of the present invention.

Examples

Figure 5:
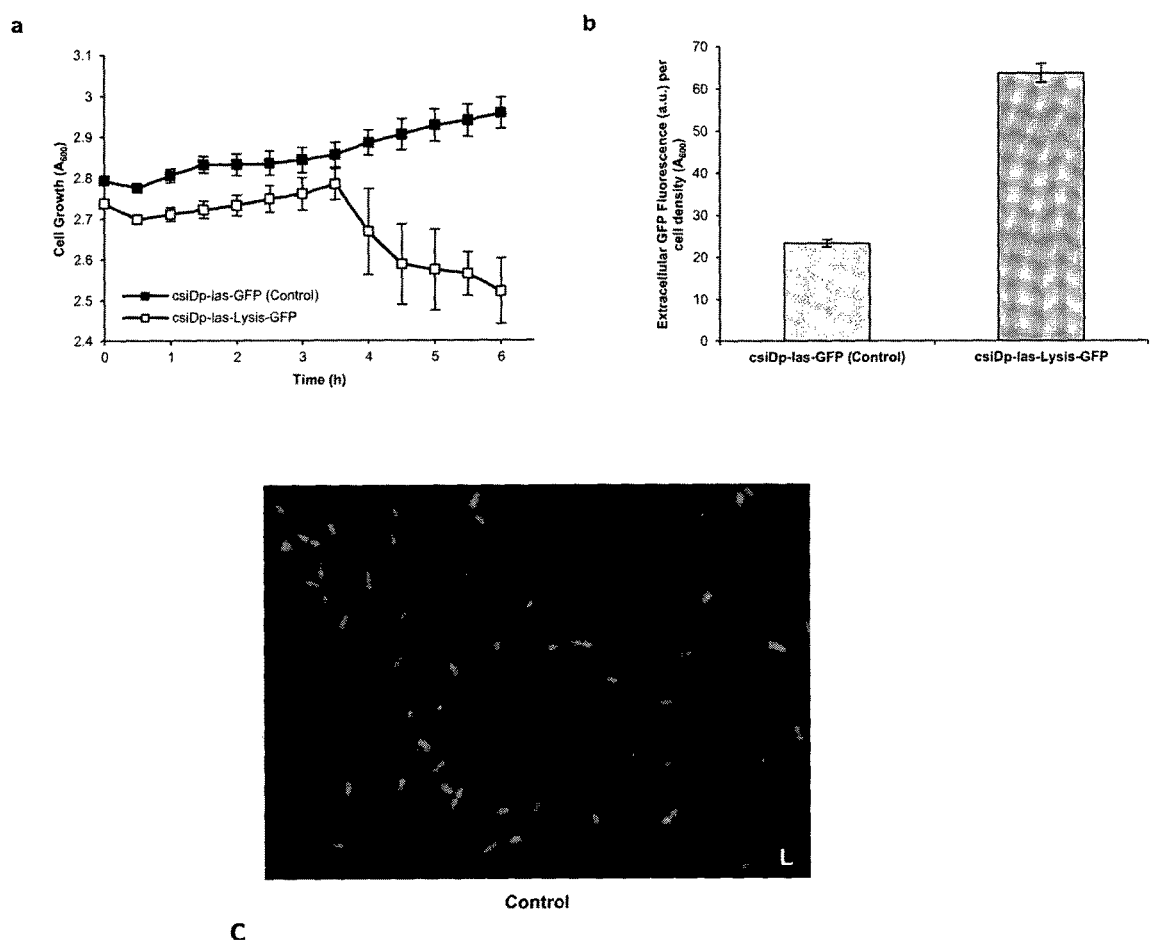
FIG. 5: (a) The lytic effect of the GFP-encoding synthetic lysis circuit (csiDp-lasQS-Lysis-GFP) was compared against the control (csiDp-las-GFP) after stationary phase was reached. Absorbance at 600 nm was then measured for 6 hours. The synthetic lysis system reduced the absorbance measurement (relative to control) after 3.5 hours. (b) Both the GFP expressing constructs had their extracellular GFP quantitated via the microplate fluorescence assay. Cells bearing the synthetic lysis system released nearly 3-folds more GFP than the control. (c) Both the control cells and the cells bearing csiDp-lasQS-Lysis-GFP were stained with propidium iodide for membrane damage assessment. It appeared that a considerable portion of the cells bearing csiDp-lasQS-Lysis-GFP were stained with red fluorescent propidium iodide, indicating membrane damage.

To evaluate the performance of the lysis genetic circuit of the present invention, a GFP-encoding lysis genetic circuit (csiDp-lasQS-Lysis-GFP) is used as a test construct, and the transducer-switch system with GFP (csiDp-lasQS-GFP), which was assessed in FIG. 4, as control. FIG. 5a shows that upon reaching stationary phase, the growth of E. coli bearing the lysis genetic circuit began to decrease, indicating cell lysis. To validate this lysis effect, the amount of GFP released into the extracellular medium is quantified, and the lysis genetic circuit with the control is compared. FIG. 5b indicates that with E7 lysis protein, the synthetic lysis system released a nearly 3-fold higher GFP into the extracellular medium, relative to the control. To further demonstrate the lysis effect, the E. coli cells is stained with propidium iodide, a widely used dye molecule that labels bacteria that have damaged membrane. Membrane-damaged cells stained with propidium iodide produce fluorescent red at excitation and emission wavelengths of 490 and 635 nm, respectively. Fluorescent microscopy data confirmed that a considerable number of the E. coli cells bearing the lysis genetic circuit underwent membrane damage, as illustrated in FIG. 5c (right), in contrast to the control cells (FIG. 5c, left).

Figure 6:
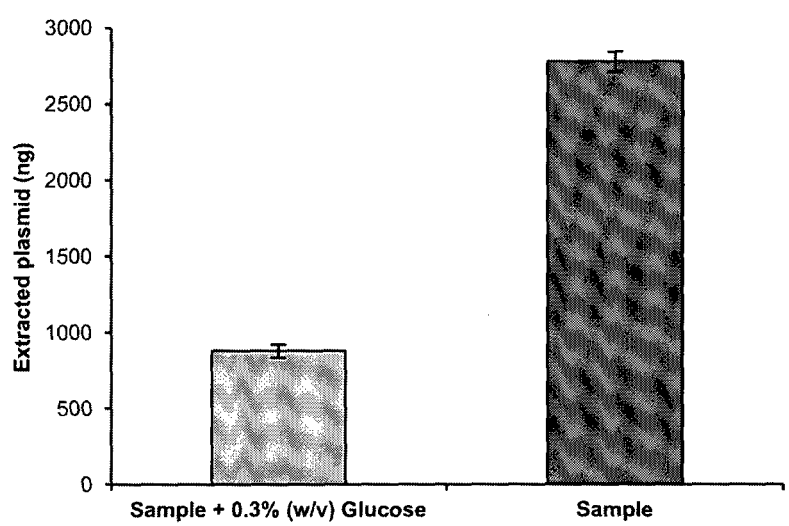
FIG. 6: (a) Effect of glucose on the amount of macromolecular product released. DNA plasmid extracted from the extracellular medium of the cells growing with and without glucose were compared. (b) Extracted DNA samples were ran in 0.8% (w/v) agarose gel at 120V for 20 mins, using Thermo Scientific GeneRuler 1 kb DNA ladder as marker. No band was observed for sample repressed with 0.3% (w/v) glucose, highlighting the effect of 0.3% (w/v) glucose on the synthetic lysis system. Expected band size of pSB1k3-RFP is ~3 kb. Non-linearized plasmid would appear lower than the expected band size in the agarose gel.
Figure 6:
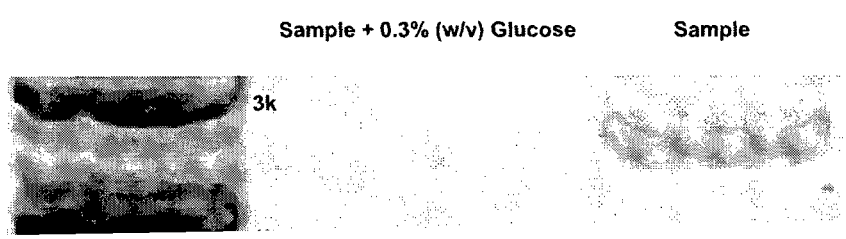

To demonstrate that the lysis genetic circuit (csiDp-lasQS-Lysis) could be harnessed for effective release of macromolecule products and controllable by glucose concentration, the performance of the lysis genetic circuit in E. coli using plasmid DNA extraction as a testbed, an essential molecular biology technique required for DNA modification, cloning and expression in biological engineering is evaluated. Since the lysis genetic circuit is present in low copy number vector (~4-6 molecules per cells) which may be difficult to quantitate and visualize in a DNA electrophoresis gel, the cells together with a high copy number test plasmid, pSB1K3-RFP (~100-300 molecules per cells) which carries a different resistance marker from the lysis genetic circuit is co-transformed. The cells is grown in LB medium containing 0.3% (w/v) glucose to prevent lysis activation, as suggested by the GFP-encoding test construct in earlier test, to stationary phase followed by medium replacement with fresh LB medium supplemented with 0 and 0.3% (w/v) glucose. The quantity and quality of the DNA plasmid which was automatic released into the supernatant after the E. coli cells were incubated for an additional 8 hours is quantified. As a control, the cells growing in 0.3% (w/v) glucose were used. FIG. 6a shows that plasmid DNA from the cells growing in 0% (w/v) glucose LB was released at a 3-fold higher into the medium upon stationary phase, than the cells growing in 0.3% (w/v) glucose. Further, absorbance measurement at 260 nm and 280 nm indicated that the plasmid released from the cells was of a good purity with an $A_{260}/A_{280}$ ratio of 1.78±0.12. Usually, an $A_{260}/A_{280}$ ratio of 1.8-2.0 indicates a pure nucleic acid sample. To ensure that the extracted DNA was indeed the expected plasmid DNA (pSB1K3-RFP), the samples is run in 0.8% (w/v) agarose DNA electrophoresis gel (FIG. 6b), and PCR is conducted using verification primers, VF2 and VR from BioBrick parts registry. Both the DNA electrophoresis gel and the PCR results affirmed that the extracted plasmid was indeed pSB1K3-RFP. Taken together, this result implies that the engineered E. coli allows users to manipulate lysis timing through glucose input, and offers a more economical means for collecting plasmids without the usage of chemical, enzymatic and/or mechanical lysis methods.

Figure 7:
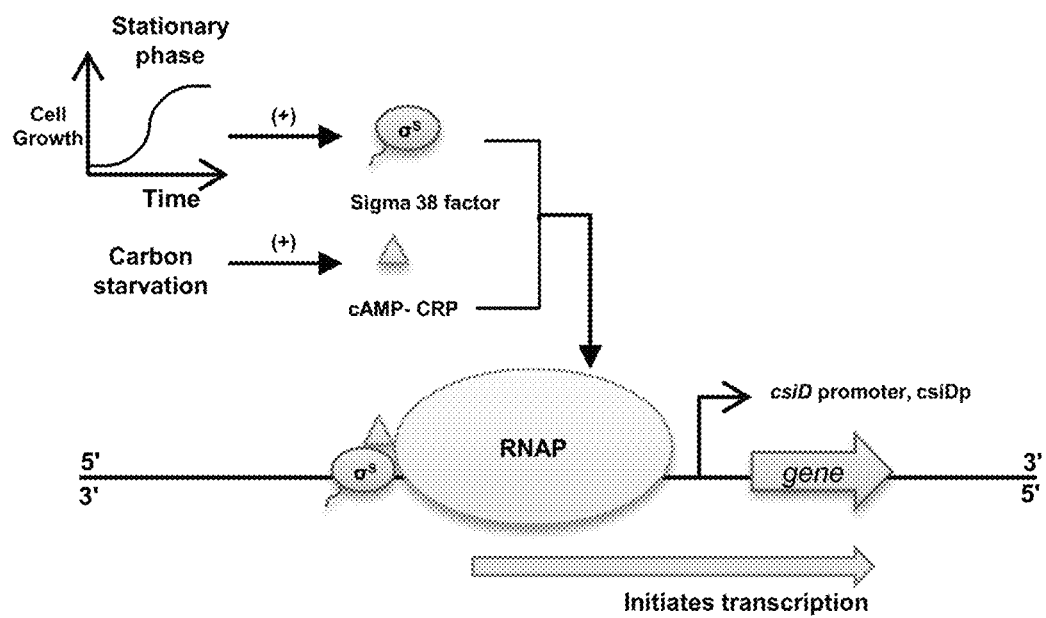
FIG. 7: A schematic illustration of how the csiDp transducer acts as an "AND" gate where two signal molecules RpoS and cAMP-CRP complex are required to activate the csiDp transducer.

In the design of the synthetic lysis system, a transducer (csiDp) from the host E. coli and a heterologous switch (las quorum sensing system) from separate organism, P. aeruginosa are utilized. The csiDp, which is derived from the host organism, is used as a transducer, rather than a switch. The reason for this arrangement is to ensure that the output lytic protein expression would not be affected by the variations in the input. By having an independent expression system, the lytic protein expression is free from interfering host machinery, and would perform consistently despite varying glucose inputs. The csiDp transducer, which is responsible for sensing the growth stage of the host cell as well as the amount of carbon source in the media, is regulated by stress sigma 38 factor (RpoS). RpoS is a transcription factor that is produced only during stationary phase [12], thus ensuring that csiDp would not be activated during the growing stage (log phase) of the cells. Stationary phase is desired as it allows the cells to reach a high cell density for maximal product extraction. Further, to make the triggering conditions more specific, the csiDp responds to the carbon starvation signal, CRP-cAMP complex. This signal is generated during carbon exhaustion. The indication of carbon exhaustion indicates that the nutrients in the growth media have depleted, and the cells could grow no further, hence serving as an indicator for the timely macromolecule release. The presence of both RpoS and CRP-cAMP creates a "AND" logic gate conditions for the activation of the csiDp transducer (FIG. 7).

Las Quorum Sensing System as an Independent Switch.

Figure 8:
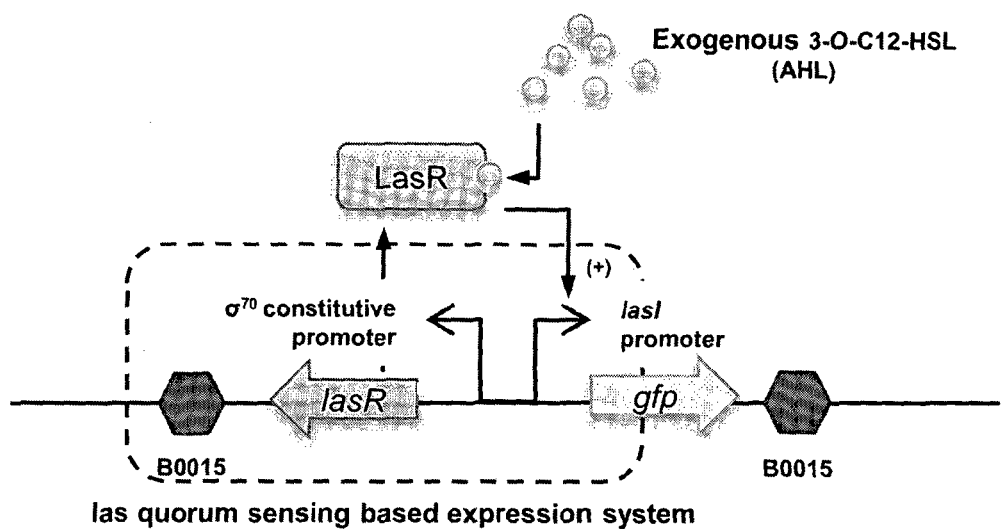
FIG. 8: Characterization of las quorum sensing system. Exogenous AHL molecules were added in range of $10^{-5}$ M-$10^{-10}$ M. Once the nano-molar AHL threshold is reached, the lytic output (indicated hereby the green fluorescence protein, GFP) is consistent.
Figure 8:
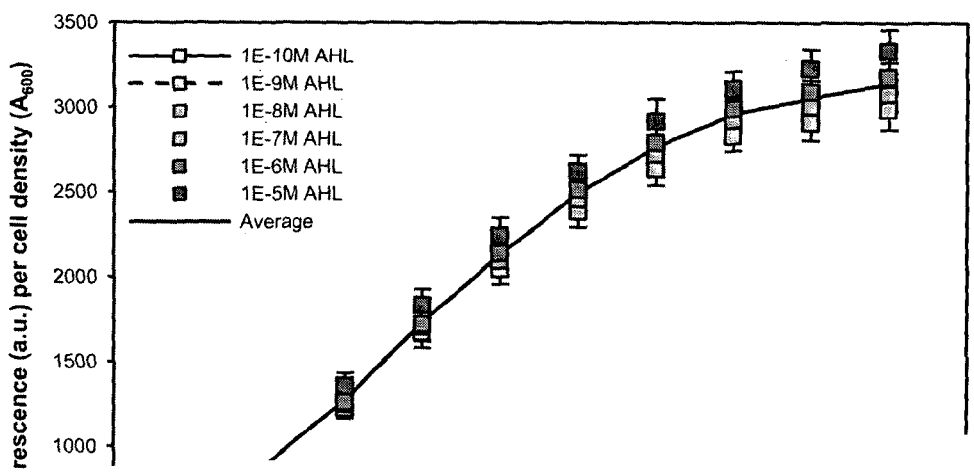

The las quorum sensing system, which is derived from P. aeruginosa, behaves similarly to a well-studied V. fisheri's lux system, with the exception of the type of signaling AHL involved. The las quorum sensing system senses the concentration of N-3-oxo-dodecanoyl-L-homoserine lactone (3-O—C12-HSL), produced by the product of lasI gene. las quorum sensing system was selected as a switch due to its ability to produce a standard and consistent output once the threshold AHL concentration is reached (FIG. 8)

Genetic Circuit Layout.

Figure 9:
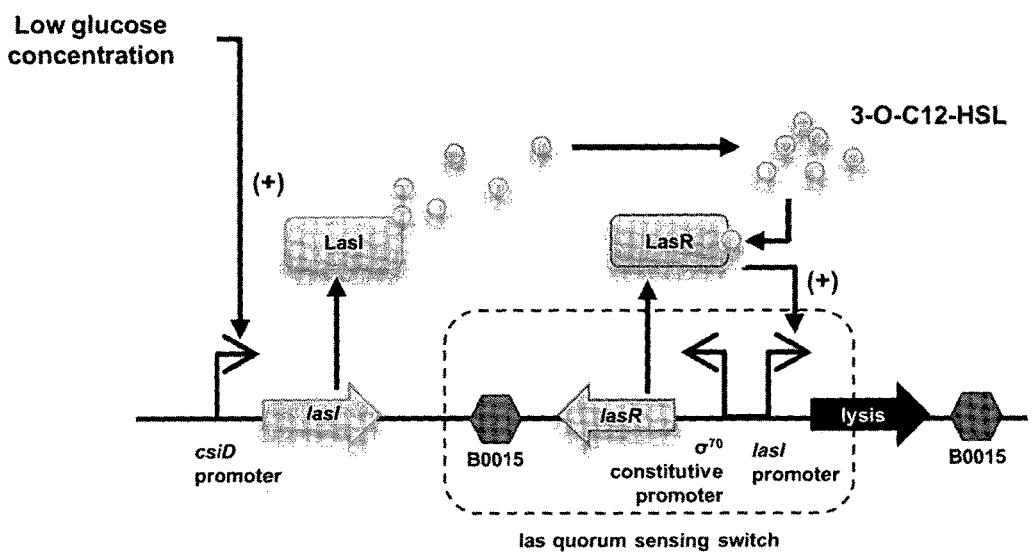
FIG. 9: Genetic circuit design of the controllable synthetic lysis system for E. coli.

In this invention, the lasI gene is placed under the control of csiDp to regulate the expression of AHL synthetase (FIG. 9). Though different amounts of LasI may be produced in response to varying glucose inputs, the threshold concentration to las quorum sensing system remains the same, ensuring consistent performance.

SEQUENCE LISTING

The sequences mentioned throughout the specification refer to the following:

SEQ ID NO. 1 (csiD promoter nucleic acid seq)
SEQ ID NO. 2 (cAMP-CRP consensus binding site nucleic acid seq)
SEQ ID NO. 3 (LasI promoter nucleic acid seq)
SEQ ID NO. 4 (LasI gene coding nucleic acid seq)
SEQ ID NO. 5 (lasR gene coding nucleic acid seq)

REFERENCES

[1] D. V. Goeddel, D. G. Kleid, F. Bolivar, H. L. Heyneker, D. G. Yansura, R. Crea, T. Hirose, A. Kraszewski, K. Itakura, and A. D. Riggs, "Expression in *Escherichia coli* of chemically synthesized genes for human insulin," *Proc Natl Acad Sci USA*, vol. 76, (no. 1), pp. 106-10, January 1979.

[2] Y. K. Jung and S. Y. Lee, "Efficient production of polylactic acid and its copolymers by metabolically engineered *Escherichia coli*," *J Biotechnol*, vol. 151, (no. 1), pp. 94-101, Jan. 10 2011.

[3] L. Pasotti, S. Zucca, M. Lupotto, M. G. Cusella De Angelis, and P. Magni, "Characterization of a synthetic bacterial self-destruction device for programmed cell death and for recombinant proteins release," *J Biol Eng*, vol. 5, pp. 8, 2011.

[4] M. Morita, K. Asami, Y. Tanji, and H. Unno, "Programmed *Escherichia coli* Cell Lysis by Expression of Cloned T4 Phage Lysis Genes," *Biotechnology Progress*, vol. 17, (no. 3), pp. 573-576, 2001.

[5] T. Park, D. K. Struck, J. F. Deaton, and R. Young, "Topological dynamics of holins in programmed bacterial lysis," *Proceedings of the National Academy of Sciences*, vol. 103, (no. 52), pp. 19713-19718, Dec. 26, 2006 2006.

[6] J. Yun, J. Park, N. Park, S. Kang, and S. Ryu, "Development of a novel vector system for programmed cell lysis in *Escherichia coli*," *J Microbiol Biotechnol*, vol. 17, (no. 7), pp. 1162-8, July 2007.

[7] J. Y. Jeong, Y. J. Kim, N. Cho, D. Shin, T. W. Nam, S. Ryu, and Y. J. Seok, "Expression of ptsG encoding the major glucose transporter is regulated by ArcA in *Escherichia coli*," *J Biol Chem*, vol. 279, (no. 37), pp. 38513-8, Sep. 10, 2004.

[8] W. Rungrassamee, X. Liu, and P. J. Pomposiello, "Activation of glucose transport under oxidative stress in *Escherichia coli*," *Arch Microbiol*, vol. 190, (no. 1), pp. 41-9, July 2008.

[9] S. Nocadello and E. Swennen, "The new pLAI (lux regulon based auto-inducible) expression system for recombinant protein production in *Escherichia coli*," *Microbial Cell Factories*, vol. 11, (no. 1), pp. 3, 2012.

[10] C. Marschall, V. Labrousse, M. Kreimer, D. Weichart, A. Kolb, and R. Hengge-Aronis, "Molecular analysis of the regulation of csiD, a carbon starvation-inducible gene in *Escherichia coli* that is exclusively dependent on σS and requires activation by cAMP-CRP," *Journal of Molecular Biology*, vol. 276, (no. 2), pp. 339-353, 1998.

[11] M. Metzner, J. Germer, and R. Hengge, "Multiple stress signal integration in the regulation of the complex σ-dependent csiD-ygaF-gabDTP operon in *Escherichia coli*," *Molecular Microbiology*, vol. 51, (no. 3), pp. 799-811, 2004.

[12] A. Battesti, N. Majdalani, and S. Gottesman, "The RpoS-Mediated General Stress Response in *Escherichia coli*," *Annual Review of Microbiology*, vol. 65, (no. 1), pp. 189-213, 2011.

[13] E. C. Pesci, J. P. Pearson, P. C. Seed, and B. H. Iglewski, "Regulation of las and rhl quorum sensing in *Pseudomonas aeruginosa*," *J Bacteriol*, vol. 179, (no. 10), pp. 3127-32, May 1997.

[14] J. R. Swartz, "Advances in *Escherichia coli* production of therapeutic proteins," *Curr Opin Biotechnol*, vol. 12, (no. 2), pp. 195-201, April 2001.

[15] H. Liu, Y. Xu, Z. Zheng, and D. Liu, "1,3-Propanediol and its copolymers: research, development and industrialization," *Biotechnol J*, vol. 5, (no. 11), pp. 1137-48, November 2010.

[16] P. I. Nikel, M. J. Pettinari, M. A. Galvagno, and B. S. Mendez, "Poly(3-hydroxybutyrate) synthesis from glycerol by a recombinant *Escherichia coli* arcA mutant in fed-batch microaerobic cultures," *Appl Microbiol Biotechnol*, vol. 77, (no. 6), pp. 1337-43, January 2008.

What is claimed is:

1. An expression system comprising one or more nucleic acid constructs, wherein the one or more nucleic acid constructs comprise:
   (i) a first gene encoding for one or more protein(s) that activate a quorum sensing system; wherein the quorum sensing system is one or more of an rhl quorum sensing system, an las quorum sensing system, and combinations thereof; and
   (ii) a second gene encoding for one or more bacteriophage lytic protein(s) capable of forming a lesion in a host cell's membrane;
   wherein the first gene is under control of a first promoter and the second gene is under control of a second promoter, wherein the first promoter controlling the first gene is a carbon starvation-induced promoter and the second promoter is a quorum sensing system promoter induced by the quorum sensing system activated by one or more protein(s) encoded by the first gene.

2. The expression system of claim 1, wherein the first promoter is a glucose-dependent carbon-starvation induced promoter.

3. The expression system of claim 1, wherein the first promoter is a stationary growth phase induced promoter.

4. The expression system of claim 1, wherein the first promoter is the csiD promoter (csiDp) from *E. coli*.

5. The expression system of claim 3, wherein the carbon starvation signaling molecule activating the first promoter is cAMP-CRP complex and the stationary phase signaling molecule is stress sigma 38 factor (RpoS).

6. The expression system of claim 1, wherein the first gene encodes for:
   (i) one or more signaling molecules capable of activating said quorum sensing system upon reaching a threshold concentration; or
   (ii) one or more enzymes that produce said signaling molecules of (i).

7. The expression system of claim 6, wherein the one or more enzymes that produce said signaling molecules comprise N-acyl-homoserine-lactone synthetase (AHL synthetase) and the signaling molecule is N-acyl-homoserine-lactone (AHL).

8. The expression system of claim 1, wherein the second promoter is induced upon reaching a threshold concentration of a signaling molecule of the quorum sensing system activated by one or more protein(s) encoded by the first gene.

9. The expression system of claim 1, wherein the quorum sensing system is from *Pseudomonas aeruginosa*.

10. The expression system of claim 1, wherein the second promoter is the lasI gene promoter from *Pseudomonas aeruginosa*.

11. The expression system of claim 10, wherein the lasI gene promoter is activated by AHL produced by the first gene product upon reaching a certain AHL threshold concentration.

12. The expression system of claim 1, wherein the first gene is the lasI gene and encodes the acylhomoserine lactone (AHL) synthase LasI that produces N-3-oxo-dodecanoyl-L-homoserine lactone (3-O—C12-HSL) from the substrates 3-oxo-C12-acyl-carrier protein (acyl-ACP) and S-adenosyl-L-methionine.

13. The expression system of claim 1 comprising two or more nucleic acid constructs, wherein the first gene and the first promoter are located on a first nucleic acid construct, and the second gene and the second promoter are located on a second nucleic acid construct.

14. The expression system of claim 1, wherein said expression system further comprises a third gene encoding for a gene product of interest.

15. The expression system of claim 14, wherein the gene product of interest is a therapeutic or non-therapeutic protein or a biopolymer or component thereof.

16. The expression system of claim 14, wherein the third gene is located in a third nucleic acid construct.

17. A recombinant cell comprising an expression system, wherein the expression system comprises one or more nucleic acid constructs, wherein the one or more nucleic acid constructs comprise:
   (i) a first gene encoding for one or more protein(s) that activate a quorum sensing system; wherein the quorum sensing system is one or more of an rhl quorum sensing system an las c quorum sensing system, and combinations thereof; and
   (ii) a second gene encoding for one or more bacteriophage lytic protein(s) capable of forming a lesion in a host cell's membrane;
   wherein the first gene is under control of a first promoter and the second gene is under control of a second promoter, wherein the first promoter controlling the first gene is a carbon starvation-induced promoter and the second promoter is a quorum sensing system promoter induced by the quorum sensing system activated by one or more protein(s) encoded by the first gene.

18. The recombinant cell of claim 17, wherein the recombinant cell is a genetically engineered prokaryotic cell.

19. The recombinant cell of claim 17, wherein the recombinant cell is an *Escherichia coli* cell.

20. The recombinant cell of claim 17, wherein the first promoter is an autologous promoter.

21. The recombinant cell of claim 17, wherein the quorum sensing system comprises a heterologous quorum sensing system.

22. The recombinant cell of claim 17, wherein the second gene is a heterologous gene.

23. The recombinant cell of claim 17, wherein said cell further comprises a third gene encoding for a gene product of interest.

24. The recombinant cell of claim 23, wherein the gene product of interest is a therapeutic or non-therapeutic protein or a biopolymer or component thereof.

25. The recombinant cell of claim 23, wherein the third gene is located in a nucleic acid construct different from that/those hosting the first and/or second gene.

26. A method for the recombinant expression of a gene product of interest, comprising cultivating a recombinant cell under conditions that allow the expression of the gene product of interest and lysis of the recombinant cell, wherein the recombinant cell comprises an expression system, wherein the expression system comprises one or more nucleic acid constructs, wherein the one or more nucleic acid constructs comprise:
  (i) a first gene encoding for one or more protein(s) that activate a quorum sensing system, wherein the quorum sensing system is one or more of an rhl quorum sensing system, an las quorum sensing system, and combinations thereof; and
  (ii) a second gene encoding for one or more bacteriophage lytic protein(s) capable of forming a lesion in a host cell's membrane;
wherein the first gene under control of a first promoter and the second gene is under control of a second promoter, wherein the first promoter controlling the first gene is a carbon-starvation-induced promoter and the second promoter is a quorum sensing system promoter induced by the quorum sensing system activated by one or more protein(s) encoded by the first gene, and wherein said cell further comprises a third gene encoding for a gene product of interest.

27. The method of claim 26, further comprising isolating the gene product of interest from the cultivating medium after lysis of the recombinant cell has occurred.

* * * * *

UNITED STATES PATENT AND TRADEMARK OFFICE
CERTIFICATE OF CORRECTION

PATENT NO. : 9,976,116 B2  
APPLICATION NO. : 14/654263  
DATED : May 22, 2018  
INVENTOR(S) : Matthew Wook Chang et al.

It is certified that error appears in the above-identified patent and that said Letters Patent is hereby corrected as shown below:

In the Claims

Column 18, Line 39 in Claim 17:
"system an las c quorum sensing system, and combinations" should read, --system, an las quorum sensing system, and combinations--.

Signed and Sealed this
Thirtieth Day of July, 2019

Andrei Iancu
*Director of the United States Patent and Trademark Office*